(12) United States Patent
Podolski et al.

(10) Patent No.: US 10,328,022 B2
(45) Date of Patent: *Jun. 25, 2019

(54) FORMULATIONS AND METHODS FOR VAGINAL DELIVERY OF ANTIPROGESTINS

(71) Applicant: REPROS THERAPEUTICS INC., The Woodlands, TX (US)

(72) Inventors: Joseph S. Podolski, The Woodlands, TX (US); Kuang Hsu, The Woodlands, TX (US)

(73) Assignee: REPROS THERAPEUTICS INC., The Woodlands, TX (US)

( * ) Notice: Subject to any disclaimer, the term of this patent is extended or adjusted under 35 U.S.C. 154(b) by 39 days.

This patent is subject to a terminal disclaimer.

(21) Appl. No.: 14/403,141

(22) PCT Filed: May 30, 2013

(86) PCT No.: PCT/US2013/043447
§ 371 (c)(1),
(2) Date: Nov. 21, 2014

(87) PCT Pub. No.: WO2013/181449
PCT Pub. Date: Dec. 5, 2013

(65) Prior Publication Data
US 2015/0111862 A1 Apr. 23, 2015

Related U.S. Application Data

(60) Provisional application No. 61/653,674, filed on May 31, 2012.

(51) Int. Cl.
*A61K 31/573* (2006.01)
*A61K 9/48* (2006.01)
*A61K 9/00* (2006.01)

(52) U.S. Cl.
CPC .......... *A61K 9/0034* (2013.01); *A61K 9/4816* (2013.01); *A61K 9/4858* (2013.01); *A61K 31/573* (2013.01)

(58) Field of Classification Search
CPC .. A61K 9/0034; A61K 9/4816; A61K 9/4858; A61K 9/4841; A61K 31/573
See application file for complete search history.

(56) References Cited

U.S. PATENT DOCUMENTS

| 4,233,296 | A | | 11/1980 | Teutsch et al. |
| 4,508,703 | A | | 4/1985 | Redziniak et al. |
| 4,615,697 | A | | 10/1986 | Robinson |
| 4,621,023 | A | | 11/1986 | Redziniak et al. |
| 4,695,450 | A | * | 9/1987 | Bauer ............... A61K 9/107 424/455 |
| 4,954,490 | A | | 9/1990 | Cook et al. |
| 5,077,211 | A | | 12/1991 | Yarosh |
| 5,468,741 | A | | 11/1995 | Yen |
| 5,788,980 | A | * | 8/1998 | Nabahi ............... A61K 9/0036 424/430 |
| 6,020,328 | A | | 2/2000 | Cook et al. |
| 6,043,234 | A | | 3/2000 | Stockemann et al. |
| 6,451,780 | B1 | | 9/2002 | Chwalsz et al. |
| 6,455,077 | B2 | | 9/2002 | Katiyar et al. |
| 6,861,415 | B2 | | 3/2005 | Kim et al. |
| 6,900,193 | B1 | | 5/2005 | Kim et al. |
| 6,982,091 | B2 | | 1/2006 | Pauletti et al. |
| 7,417,013 | B2 | | 8/2008 | Ahmad et al. |
| 8,426,394 | B2 | | 4/2013 | Podolski |
| 8,519,004 | B2 | | 8/2013 | Podolski |
| 8,569,276 | B2 | | 10/2013 | Kim et al. |
| 8,735,381 | B2 | * | 5/2014 | Podolski ............... A61K 31/56 514/179 |
| 2002/0025951 | A1 | | 2/2002 | Kim et al. |
| 2004/0048841 | A1 | | 3/2004 | Hoffmann et al. |
| 2005/0070516 | A1 | | 3/2005 | Wilson et al. |
| 2005/0143365 | A1 | | 6/2005 | Kim et al. |
| 2006/0241125 | A1 | | 10/2006 | Bradley et al. |
| 2007/0103510 | A1 | | 5/2007 | Silverbrook |
| 2007/0213306 | A1 | | 9/2007 | Hausknecht |
| 2008/0248102 | A1 | | 10/2008 | Rajewski et al. |
| 2009/0149434 | A1 | * | 6/2009 | Podolski ............... A61K 31/56 514/179 |

(Continued)

FOREIGN PATENT DOCUMENTS

| AU | 1997/029304 B2 | 9/1999 |
| AU | 2007/327707 B2 | 7/2012 |
| CN | 1846703 | 10/2006 |

(Continued)

OTHER PUBLICATIONS

Ruddock and coworker (American Journal of Obstetrics and Gynecology vol. 199 pp. 391e1-391e7 published 2008) (Year: 2008).*
Goyeneche et al., Clinical Cancer Research vol. 13 pp. 3370-3379 (2007) (Year: 2007).*
Jurado et al., Oncology Reports vol. 22 pp. 1237-1245. Published 2009 (Year: 2009).*
Attardi, B., et al., "CDB-4124 and Its Putative Monodemthylated Metabolite, CDB-4453, are Potent Antiprogestins with Reduced Antiglucocorticoid Activity: In Vitro Comparison to Mifepristone and CDB-2914", Molecular and Cellular Endocrinology, vol. 188, No. 1-2, pp. 111-123 (Feb. 25, 2002).
Bauerfeind, I., et al., "Endocrine Agents in the Treatment of Advanced Breast Cancer," Gynakologe Aug. 1999 DE, vol. 32, No. 8, pp. 605-613 (Aug. 1999).

(Continued)

*Primary Examiner* — Timothy P Thomas
*Assistant Examiner* — George W Kosturko
(74) *Attorney, Agent, or Firm* — Morgan, Lewis & Bockius LLP; Christopher J. Betti (57) ABSTRACT

The subject matter of the present invention is pertinent to the field of vaginal delivery of pharmaceutically active agents. Embodiments of the instant invention disclose methods for treating a variety of progesterone related disorders by vaginal administration of a pullulan capsule comprising one or more antiprogestins.

6 Claims, 5 Drawing Sheets

(56) References Cited

U.S. PATENT DOCUMENTS

| | | |
|---|---|---|
| 2011/0046098 A1 | 2/2011 | Podolski |
| 2014/0163114 A1 | 6/2014 | Podolski et al. |

FOREIGN PATENT DOCUMENTS

| | | | |
|---|---|---|---|
| CN | 1950072 | 4/2007 | |
| CN | 102014923 | 4/2011 | |
| EP | 0245170 A1 | 11/1987 | |
| EP | 1593376 A1 * | 11/2005 | ........... A61K 9/4816 |
| EP | 1593376 A1 * | 11/2005 | ........... A61K 9/4816 |
| EP | 1864631 A1 * | 12/2007 | ............... A61F 5/41 |
| JP | 9-502724 | 3/1997 | |
| JP | 2000-509396 | 7/2000 | |
| JP | 2003-529604 | 7/2000 | |
| JP | 3143474 | 12/2000 | |
| JP | 2008-505718 | 2/2008 | |
| JP | 2008-509217 | 3/2008 | |
| JP | 2010-18639 | 1/2010 | |
| JP | 2010-540430 | 12/2010 | |
| WO | WO 83/03099 | 9/1983 | |
| WO | WO 95/07699 | 3/1995 | |
| WO | WO 97/41145 | 11/1997 | |
| WO | WO 98/08471 | 3/1998 | |
| WO | WO 99/45022 | 9/1999 | |
| WO | WO 00/34036 | 6/2000 | |
| WO | WO 01/18025 | 3/2001 | |
| WO | WO 01/24788 | 4/2001 | |
| WO | WO 01/74840 | 10/2001 | |
| WO | WO 0174840 A2 * | 10/2001 | ........... C07J 5/0053 |
| WO | WO 03/005954 | 1/2003 | |
| WO | WO 04/096151 | 11/2004 | |
| WO | 2005105051 | 11/2005 | |
| WO | WO 06/010097 | 1/2006 | |
| WO | WO 06/023109 | 3/2006 | |
| WO | WO 06/136462 | 12/2006 | |
| WO | WO 07/103510 | 9/2007 | |
| WO | WO 08/067086 | 6/2008 | |
| WO | WO 08/129396 | 10/2008 | |
| WO | WO 09/037704 | 3/2009 | |
| WO | WO-2009037704 A1 * | 3/2009 | ........... A61K 9/0007 |
| WO | WO 11/039680 | 4/2011 | |
| WO | WO 2011/039680 A1 | 4/2011 | |
| WO | WO 12/087389 | 6/2012 | |
| WO | WO 12/121767 | 9/2012 | |

OTHER PUBLICATIONS

Benagiano, G., et al., "Selective Progesterone Receptor Modulators 3: Use in Oncology, Endocrinology and Psychiatry," Expert Opinion on Pharmacotherapy, vol. 9, No. 14, pp. 2487-2496 (Oct. 2008).
Bouchard, P., et al., "Selective Progesterone Receptor Modulators in Reproductive Medicine: Pharmacology, Clinical Efficacy and Safety," Fertility and Sterility, vol. 96, No. 5, pp. 1175-1189 (Nov. 2011).
Brueggemeier, R. W., et al., Aromatase Inhibitors in the Treatment of Breast Cancer, Endocrine Reviews, vol. 26, No. 3, pp. 331-345 (May 2005).
Bulun, S., et al., Regulation of Aromatase Expression in Estrogen-Responsive Breast and Uterine Disease: From Bench to Treatment, Pharmacological Reviews, vol. 57, No. 3, pp. 359-383 (Sep. 2005).
Chand, A., et al., "Aromatase Expression is Increased in BRCAI Mutation Carriers," BMC Cancer, vol. 9, p. 1-9 (May 2009).
Donnez, J., et al., "Long-Term Treatment of Uterine Fibroids with Ulipristal Acetate," Fertility and Sterility, vol. 101, No. 6. pp. 1565-1573 (Jun. 2014).
Francis, Z., et al., "Contraception of the Future," Reproduction Humaine et Hormones, vol. 21, No. 1 pp. 102-116 (Mar. 2008).
Goodman and Gilman's, The Pharmacological Basis of Therapeutics, 7th Edition, p. 5 and 15 (1985).
Gupta, A., et al., "Efficacy and Mechanism of Action of Proellex, an Antiprogestin in Aromatase Overexpressing and Letrozole Resistant T47 Breast Cancer Cells," Journal of Steroid Biochemistry and Molecular Biology. vol. 133, pp. 30-42 (Jan. 2013).
Heikinheimo, O., Drug Disposition "Clinical Pharmacokinetics of Mifepristone," Clin. Pharmacokinet, No. 1, pp. 7-17 (Jul. 1997).
Heikinheimo, O., et al., "Intravaginal Administration of RU 4868 in Humans and Rats: Inadequate Absorption in Humans," Hum Reprod., vol. 2, No. 8, pp. 645-7648 (Nov. 1987) Abstract.
Horwitz, K., The Molecular Biology of RU 486. Is There a Role for Antiprogestins in the Treatment of Breast Cancer?, Endocrine Reviews, vol. 13, No. 2, pp. 146-163 (May 1992).
International Preliminary Report on Patentability of PCT/US13/066095 dated May 5, 2015.
International Preliminary Report on Patentability of PCT/US2008/078684 dated May 11, 2010.
International Preliminary Report on Patentability of PCT/US2009/041826 dated Nov. 2, 2010.
International Preliminary Report on Patentability of PCT/US2009/041795 dated Nov. 2, 2010.
International Preliminary Report on Patentability of PCT/US2009/041841 dated Nov. 2, 2010.
International Preliminary Report on Patentability of PCT/US2009/041836 dated Feb. 11, 2010.
International Preliminary Report on Patentability of PCT/US2010/50859 dated Jun. 25, 2013.
International Preliminary Report on Patentability of PCT/US2010/62068 dated Sep. 25, 2012.
International Preliminary Report on Patentability of PCT/US2013/043447 dated Dec. 2, 2014.
International Search Report of PCT/US2008/078684 dated Dec. 22, 2008.
International Search Report of PCT/US2009/041795 dated Jul. 2, 2009.
International Search Report of PCT/US2009/041826 dated Jul. 3, 2009.
International Search Report of PCT/US2009/041836 dated Jul. 3, 2009.
International Search Report of PCT/US2009/041841 dated Oct. 27, 2009.
International Search Report of PCT/US2010/62068 dated Aug. 17, 2011.
International Search Report of PCT/US2011/050859 dated Feb. 27, 2012.
International Search Report of PCT/US2013/043447 dated Aug. 13, 2013.
International Search Report of PCT/US2013/066095 dated Nov. 26, 2013.
Kawaguchi, K., et al., "Mitotic Activity in Uterine Leiomyomas During the Menstrual Cycle," America Journal Obstet. Gynecol., vol. 160, No. 3, pp. 637-641 (Mar. 1989).
Lanari, C., et al., "Antiprogestins in Breast Cancer Treatment: Are We Ready?" Endocrine Related Cancer, vol. 19, No. 3, pp. R35-R50, (Feb. 20, 2012).
Leo, Joyce, C., et al., "The Activities of Progesterone Receptor Isoform A and B are Differentially Modulated by Their Ligands in a Gene-Selective Manner,", International Journal of Cancer, vol. 122, No. 1, pp. 230-243 (Jan. 2008).
Makhsida, N., et al., "Hypogonadism and Metabolic Syndrome: Implications for Testosterone Therapy," The Journal of Urology, vol. 174, Issue 3, pp. 827-834 (Sep. 2005).
Mealy, N., et al., "CDB-4124," Drugs of the Future, vol. 29, No. 11, pp. 1133 (Nov. 2004).
Nabholtz, J. M., et al., "Anastrozole (Arimidex™) versus Tamoxifen as First-Line Therapy for Advanced Breast Cancer in Postmenopausal Women: Survival Analysis and Updated Safety Results," European Journal of Cancer, vol. 39, No. 12, pp. 1684-1689 (Aug. 2003).
Nelson, A., "Extended-Cycle Oral Contraception—A New Option for Routine Use," Treatments in Endocrinology, vol. 4, No. 3, pp. 139-145 (Jun. 2005).
Passaro, M., et al., "Luteal Phase Dose-Response Relationships of the Antiprogestin CDB-2914 in Normally Cycling Women," Human Reproduction, vol. 18, No. 9, pp. 1820-1827 (Sep. 2003).
Rose, C., et al., "An Open Randomised Trial of Second-Line Endocrine Therapy in Advanced Breast Cancer—Comparison of the

(56) References Cited

OTHER PUBLICATIONS

Aromatase Inhibitors Letrozole and Anastrozole" European Journal of Cancer, vol. 39, No. 16, pp. 2318-2327 (Nov. 2003).
Santos, A., et al., "Anastrozole as Neoadjuvant Therapy for Patients with Hormone-Dependent, Locally-Advanced Breast Cancer," Anticancer Research, vol. 24, pp. 1315-1318 (Mar. 2004).
Spitz, Irving M.,"Clinical Utility of Progesterone Receptor Moulators and Their Effect on the Endometrium," Current Opinion in Obstetrics & Gynecology, vol. 21, No. 4, pp. 318-324 (Aug. 2009).
Spitz., Irving M., "Progesterone Receptor Antagonists," Current Opinion in Investigational Drugs, vol. 7, No. 10, pp. 882-890 (Oct. 2006).
Wiehle, R., et al., "CDB-4124, A Progesterone Receptor Modulator, Inhibits Mammary Carcinogenesis by Suppressing Cell Proliferation and Inducing Apoptosis," Cancer Prevention Research, vol. 4, No. 3, pp. 414-424 (Mar. 2011).
Wiehle, Ronald, et al., "Anti-Progestins Suppress the Growth of Established Tumors Induced by 7,12-dimethylbenz(a)anthracene: comparison between RU486 and a new 21-substituted-19-nor-progestin," Oncology Reports, vol. 18, No. 1, pp. 167-174 (Jul. 2007).
Written Opinion of PCT/US09/041826 dated Oct. 28, 2010.
Written Opinion of PCT/US09/041795 dated Oct. 28, 2010.
Written Opinion of PCT/US09/041841 dated Oct. 28, 2010.
Written Opinion of PCT/US11/050859 dated Jun. 23, 2013.
Written Opinion of PCT/US2008/078684 dated May 5, 2010.
Written Opinion of PCT/US2013/066095 dated Nov. 26, 2013.
Written Opinion of PCT/US2009/041836 dated Jul. 3, 2009.
Written Opinion of PCT/US2010/62068 dated Aug. 17, 2011.
Written Opinion of PCT/US2013/043447 dated Aug. 13, 2013.
Repros Therapeutics Inc. Announces That Proellex Administered to Patients as Cyclic Therapy to Treat the Symptoms of Uterine Fibroids for Up to 30 Months Shows No Adverse Effects on the Endometrium, Drug Information Online—Drugs.com, pp. 1-2 (Jul. 2008).
U.S. Appl. No. 12/990,203—Non-Final office action dated Jun. 1, 2012.
U.S. Appl. No. 12/990,203—Notice of Allowance dated Dec. 26, 2012.
U.S. Appl. No. 12/990,210—Final Office Action dated Feb. 26, 2015.
U.S. Appl. No. 12/990,210—Non-final office action dated Aug. 7, 2013.
U.S. Appl. No. 12/990,210—Non-final office action dated Dec. 4, 2012.
U.S. Appl. No. 12/990,210—Restriction Requirement dated Apr. 24, 2012.
U.S. Appl. No. 12/245,089—Restriction Requirement dated Jun. 4, 2010.
U.S. Appl. No. 12/245,089—Non-Final Office Action dated Sep. 7, 2010.
U.S. Appl. No. 13/636,119—Restriction Requirement dated Dec. 11, 2014.
U.S. Appl. No. 13/636,119—Non-final office action dated Apr. 7, 2015.
U.S. Appl. No. 13/636,119—Final Office Action dated Jul. 9, 2015.
U.S. Appl. No. 13/636,119—Non-final Office Action dated Dec. 11, 2015.
U.S. Appl. No. 13/855,559—Notice of Allowance dated Feb. 23, 2013.
U.S. Appl. No. 13/997,097—Non-final office action dated Sep. 22, 2014.
U.S. Appl. No. 14/664,518—Non-final office action dated May 18, 2016.
U.S. Appl. No. 14/286,535—Non-final office action dated Nov. 6, 2015.
U.S. Appl. No. 14/440,023—Non-final office action dated Feb. 16, 2016.
U.S. Appl. No. 14/403,141—Restriction Requirement dated Mar. 22, 2016.
International Search Report of PCT/US2013/043447 dated Aug. 12, 2013.
Written Opinion of PCT/US2013/043447 dated Aug. 12, 2013.
Alexander, et al., "Why consider vaginal drug administration?" Fertility and Sterlility, vol. 82, No. 1, pp. 1-12 (2004).
Bulun, S., "Uterine Fibroids," The New England Journal of Medicine, vol. 369, pp. 1344-1355 (2013).
Eisenberg, Ester, MD, "Endometriosis" The Merck Manuals Online Library, at http://www.merckmanuals.com/professional/gynecology-and-obstetrics/endometriosis/endometriosis, revised Feb. 2013.
European Search Report for European Application No. 15179121.7 dated Nov. 4, 2015.
U.S. Appl. No. 13/636,119—Final Office Action dated Sep. 19, 2016.
U.S. Appl. No. 14/286,525—Final Office Action dated Aug. 31, 2016.
Chilean Patent Application No. 201403232, Office Action, dated Sep. 1, 2017, 7 pages.
Chinese Patent Application No. 201380028413.4, Third Office Action, dated Jul. 31, 2017, 17 pages.
Chinese Patent Application No. 201380028413.4, Fourth Office Action, dated Jan. 31, 2018, 3 pages.
Eurasian Patent Application No. 201492290, Office Action, dated Mar. 23, 2017, 8 pages.
European Patent Application No. 13728632.4, Communication Pursuant to Article 94(3), 9 pages.
Indonesian Patent Application No. P-00201408203, Office Action dated Aug. 22, 2017, 2 pages.
Japanese Patent Application No. 2015-515205, Official Action dated Nov. 29, 2017, 2 pages.
Japanese Patent Application No. 2015-515205, Notice of Reasons for Rejection dated Mar. 27, 2017, 8 pages.
Thailand Patent Application No. 1401006926, Notice from the Registrar, dated May 7, 2016, 2 pages.
Ukrainian Patent Application No. 201414106, Official Action dated Dec. 1, 2016, 10 pages.
Eurasian Patent Application No. 201492290, Office Action dated Dec. 26, 2016, 4 pages.
Eurasian Patent Application No. 201492290, Notice of Allowance, dated Oct. 23, 2017, 5 pages.
Chinese Patent Application No. 201380028413.4, Notice of Allowance, dated Apr. 27, 2018, 4 pages.
Japanese Patent Application No. 2015-515205, Notice of Allowance, dated Apr. 25, 2018, 2 pages.

\* cited by examiner

FORMULATIONS AND METHODS FOR VAGINAL DELIVERY OF ANTIPROGESTINS

CROSS-REFERENCE TO RELATED APPLICATIONS

This application claims the benefit of U.S. Provisional Application No. 61/653,674 filed May 31, 2012, the contents of which are incorporated herein by reference.

FIELD OF THE INVENTION

In several embodiments, the present invention relates to mucoadhesive pharmaceutical compositions and their use for local administration of active agents such as antiprogestins to the vaginal mucosa. In related embodiments, the mucoadhesive compositions are administered for the treatment of a variety of progesterone related conditions.

BACKGROUND OF THE INVENTION

The effect of the steroid hormone progesterone on the reproductive system has been well-documented. For example, progesterone is vital to establishing and maintaining pregnancy and exerts actions on various tissues of the reproductive system. The action of progesterone on tissues outside the reproductive system has been reported but is less well characterized.

Antiprogestins, compounds which inhibit the action of progesterone, have considerable potential for use in the pharmacological regulation of fertility and a variety of conditions and diseases such as breast cancer and endometriosis. The first reported antiprogestin, mifepristone (RU 486), is one of a number of 19-nortestsosterone derivatives with strong affinity for both the progesterone and glucocorticoid receptors and with antiprogestational and antiglucocorticoid activity. A variety of antiprogestins based on the 19-norprogesterone backbone have also been synthesized.

Several drawbacks are associated with the use of known antiprogestins, rendering them less than ideal for chronic administration, particularly when delivered orally. If these and other limitations associated with antiprogestin treatment could be improved, a significant advance in the treatment of hormone-dependent disorders would result.

SUMMARY OF THE INVENTION

In one embodiment, the present invention provides a mucoadhesive capsule comprising pullulan and a capsule fill formulation comprising an active agent, preferably an antiprogestin and one or more excipients for delivering the active agent to the vaginal mucosa.

In other embodiments, the present invention provides methods for the treatment of a variety of progesterone related conditions in a patient in need of such treatment by administering a mucoadhesive capsule comprising pullulan and a capsule fill formulation comprising an antiprogestin and one or more excipients to the vaginal mucosa of the patient.

In other embodiments, the present invention provides a kit comprising a mucoadhesive capsule comprising pullulan and a capsule fill formulation comprising an active agent, preferably an anitprogestin and one or more excipients for delivering the agent to the vaginal mucosa in combination with an vaginal applicator.

Progesterone-related conditions that may be treated with the mucoadhesive capsules of the invention include, without limitation, endometriosis and pain associated therewith, adenomyosis, endometriomas of the ovary, dysmenorrhea, endocrine hormone-dependent tumors, uterine fibroids, endometrial hyperproliferation, ovarian cancer, cervical cancer and breast cancer. Compositions of the instant invention may also be used to induce menses, to induce labor and for contraception.

BRIEF DESCRIPTION OF THE DRAWINGS

FIG. 4A-B illustrates pharmacokinetic data observed over a 24 hour period in rabbits following the last of 10 daily doses of 12 mg CDB-4124 delivered vaginally. Panel A illustrates CDB-4124; Panel B illustrates CDB-4453.

DETAILED DESCRIPTION OF THE INVENTION

While the present invention is capable of being embodied in various forms, the description below of several embodiments is made with the understanding that the present disclosure is to be considered as an exemplification of the invention, and is not intended to limit the invention to the specific embodiments illustrated. Headings are provided for convenience only and are not to be construed to limit the invention in any way. Embodiments illustrated under any heading may be combined with embodiments illustrated under any other heading.

It is to be understood that any ranges, ratios and ranges of ratios that can be formed by any of the numbers or data present herein represent further embodiments of the present invention. This includes ranges that can be formed that do or do not include a finite upper and/or lower boundary. Accordingly, the skilled person will appreciate that many such ratios, ranges and ranges of ratios can be unambiguously derived form the data and numbers presented herein and all represent embodiments of the invention.

Before the present compounds, compositions and methods are disclosed and described, it is to be understood that the terminology used herein is for the purpose of describing particular embodiments only and is not intended to be limiting. It must be noted that, as used in the present specification and the appended claims, the singular forms "a," "an" and "the" include plural referents unless the context clearly dictates otherwise.

Definitions

The term "capsule" refers to a hard shell pharmaceutical capsule. The capsule consists of a body and cap and may comprise a fill formulation containing a pharmacologically active agent.

The term "oral" administration means that the active agent is in a formulation designed to be ingested, i.e. designed to be delivered to the gastrointestinal system for absorption.

The term "effective dosage" means an amount of the composition's active component sufficient to treat a particular condition.

The term "selective progesterone receptor modulators" means compounds that affect functions of progesterone receptor in a tissue-specific manner. The compounds act as progesterone receptor antagonists in some tissues (for example, in breast tissue) and as progesterone receptor agonists in other tissues (for example, in the uterus).

The term "treat" or "treatment" as used herein refers to any treatment of any progesterone-dependent disorder or disease, and includes, but is not limited to, inhibiting the disorder or disease arresting the development of the disorder or disease; relieving the disorder or disease, for example, causing regression of the disorder or disease; or relieving the condition caused by the disease or disorder, relieving the symptoms of the disease or disorder.

The term "prevent" or "prevention," in relation to a progesterone-dependent disorder or disease, means preventing the onset of disorder or disease development if none had occurred, or preventing further disorder or disease development if the disorder or disease was already present. For example, compositions of the present invention may be used to prevent the recurrence of tumors. Recurrence of tumors may occur because of residual microscopic groups or nests of tumor cells which subsequently expand into clinically detectable tumors.

The term "progesterone agonist" means a compound that binds to a progesterone receptor and mimics the action of the natural hormone.

The term "progesterone antagonist" means a compound that binds to a progesterone receptor and inhibits the effect of progesterone.

In several embodiments, the present invention relates to methods of administering an active agent to the vaginal mucosa utilizing a capsule comprising pullulan and a capsule fill formulation comprising the active agent and one or more excipients.

In preferred embodiments, the present invention relates to methods of treating a progesterone related condition by vaginal administration of a mucoadhesive capsule comprising pullulan and a capsule fill formulation comprising an antiprogestin and one or more excipients to the vaginal mucosa of the patient.

Pullulan is a linear, water soluble polysaccharide polymer consisting of maltotriose units connected to each other by an α-1,6 glycosidic bond. The three glucose units in each maltotriose unit are connected by an α-1,4 glycosidic bond. The linkage pattern of pullulan is responsible for the adhesive properties of the polysaccharide and its capacity for forming fibers and oxygen-impermeable films. Pullulan is produced from starch by the fungus *Aureobasidium pullulans* and can be produced commercially by batch fermentation as described in Leathers, Appl. Microbiol. Biotechol., 62:468-473 (2003).

Capsules

Capsules suitable for use according to the invention include, without limitation NPcaps® available from Capsugel which contain pullulan, carageenan and potassium chloride, as well as capsules described in U.S. Pat. No. 8,105,625 and US Patent Application Publication No. 2005/0249676, the contents of each of which are incorporated herein by reference.

In one aspect, capsules for use according to the invention comprise pullulan with a molecular weight between about 50 to 500 kDa, between 100 to 400 kDa, between about 150 to 300 kDa and preferably between about 180 and 250 kDa.

In another aspect, capsules for use according to the invention comprise pullulan from about 50% to about 100% by weight (unfilled capsule). In other aspects, the capsules comprise about 60 to 90 or 70 to 90, or 80 to 90 wt % pullulan. Preferably the capsules comprise about 85 to 90 wt % pullulan.

Capsules for use according to the invention may further comprise (in addition to pullulan), without limitation, one or more gelling agents (e.g. hydrocolloids or polysaccharides such as alginates, agar gum, guar gum, carob, carrageenan, tara gum, gum arabic, pectin, xanthan and the like); salts comprising cations such as $K^+$, $Li^+$, $Na^+$, $NH4^+$, $Ca^{2+}$, $Mg^{2+}$; and/or surfactants such as sodium lauryl sulphate, dioctyl sodium sulfosuccinate, benzalkonium chloride, benzethonium chloride, cetrimide, fatty acid sugar esters, glycerl monooleate, polyoxyethylene sorbitan fatty acid esters, polyvinylalcohol, dimethylpolysiloxan, sorbitan esters or lecithin, as described in US Patent Application Publication No. 2005/0249676.

Capsules for use according to the invention may further comprise one or more plasticizing agents (e.g. glycerol, propylene glycol, polyvinyl alcohol, sorbitol, maltitol and the like); dissolution enhancing agents (e.g. maltose, lactose, sorbitol, mannitol, xylitol, maltitol and the like); strengthening agents (e.g. polydextrose, cellulose, maltodextrin, gelatin, gums and the like); colorants, and/or opacifiers as described in U.S. Pat. No. 8,105,625.

In a preferred embodiment, the capsule comprises pullulan in an amount of 85% to 90% by weight, potassium chloride in an amount of 1.0% to 1.5% by weight, carrageenan in an amount of 0.1% to 0.4% by weight, one or more surfactants in an amount of 0.1% to 0.2% by weight and water in an amount of 10% to 15% by weight.

In a particularly preferred embodiment, the capsule comprises pullulan in an amount of 86.3% by weight, potassium chloride in an amount of 1.32% by weight, carrageenan in an amount of 0.27% by weight, surfactants selected from sugar esters, sorbitan monolaurate and combinations thereof in an amount of 0.15% by weight and water in an amount of 12% by weight.

In another aspect, the pullulan capsule provides a continual release of the active agent at a substantially constant rate over a period of time (i.e. a steady release of the active agent) to the subject. The present inventors have discovered that capsules comprising pullulan are surprisingly advantageous for vaginal delivery of active agents. In particular, pullulan-based capsules are a safe, effective and convenient vehicle for delivering active agents to the vaginal mucosa. The present inventors have discovered that pullulan capsules adhere to the vaginal mucosa, ensuring that the capsules remain the in vagina at a desired location for the duration of drug delivery. Moreover, due in part to the solubility of pullulan, no residual capsule is left in the vagina after release of the drug, unlike conventional gelatin capsules. The present inventors surprisingly discovered that, when used as a vaginal delivery device, pullulan capsules effect a continual release of active agents at a substantially constant rate maintaining a low Cmax (peak concentration) of the active agent and ensuring a high local concentration of the drug. Thus, sustained levels of the active agent are delivered to the vaginal mucosa while systemic concentrations are minimized.

The capsule fill formulation may comprise any active agent. Preferably, the capsule fill formulation comprises an antiprogestin which may be a pure antiprogestin or a selective progesterone receptor modulator.

The capsule fill formulation may further contain one or more excipients. Appropriate excipients can be selected based on considerations including without limitation the active agent to be administered and the dosage. Excipients can function as bulking agents, release modifiers, wetting agents, tonicity agents or combinations thereof. For example, excipients may include hydrophilic excipients such as water soluble synthetic and natural polymers including without limitation polyethylene glycol (PEG), polyvinyl pyyrolidone, polymethacrylates, polylysine, polyvinyl alcohol, albumin, alginate, gelatin, chitosan, cellulose, ficoll, starchy, hydroxyethyl cellulose, hydroxypropyl cellulose, hyaluronic acid, carboxyethyl cellulose, carboxymethyl cellulose, dextran sulfate and derivatives thereof. Particular hydrophilic polymers for use in capsule fill formulations may be based on factors such as molecular weight, hydrophilicity and visocity. Hydrophilic polymers may be used as bulking or wetting agents.

Excipients may also include lipids such as, without limitation, one or a mixture of different grades of Gelucire, Labrafil®, Labrasol® and the like. Gelcuire compositions are amphiphilic inert polygycolized glycerides which form micelles in aqueous media. They are identified by their melting point (degrees Celsius)/HLB (hydrophile-lipophile balance) value. Particularly preferred Gelucire compositions for use in the capsules are Gelucire 44/14 (lauroyl polyoxyl-32 glycerides) and Gelucire 50/13 (stearoyl polyoxyl-32 glycerides).

In a preferred embodiment, the fill formulation comprises a pharmaceutically active compound, preferably CDB-4124, and excipients Gelucire 44/14 and PEG. In related aspects, Gelucire 44/14 is present as between 50% and 90%, preferably about 75% excipient w/w and PEG is present as between 50% and 10%, preferably about 25% excipient w/w. In particularly preferred embodiment, the fill formulation comprises CDB-4124 and excipients consisting of 74.13% (w/w) Gelucire and 25.87% PEG 400.

In particularly preferred embodiments, the capsule fill formulation consists of or consists essentially of a pharmaceutically active agent, preferably CDB-4124, and about 100% w/w PEG 1000 as excipient. Optionally, 0.02% butylated hydroxytoluene is also present at 0.02% excipient w/w (as antioxidant).

In other preferred embodiments, the capsule fill formulation comprises a pharmaceutically active agent, preferably CDB-4124, and excipients comprising 30% to 60% w/w Wecobee M (fatty acid ester), 30% to 60% w/w PEG 1000 and 0.1% to 5% w/w lecithin. In a related embodiment, the capsule fill formulation comprises CDB-4124 as active agent and excipients consisting of about 50% (e.g. 50.1%) w/w Wecobee M, about 50% (e.g. 49.4%) w/w PEG 1000 and about 0.5% w/w lecithin.

Excipients may also include sugars such as mannitol, sorbitol, xylitol, glucitol, ducitol, inositol, arabinitol, arabitol, galactitol, iditol, allitol, fructose, sorbose, glucose, xylose, trehalose, dextrose, galactose, talose, ribose, arabinose, sucrose, maltose, lactose, fucose, matotriose, and the like. The amount of sugar may be adjusted to provide osmolality or wetting.

Wetting agents can be used in the capsule fill drug formulation to facilitate water ingress into the capsule and wetting of the active agent and include gelatin, casein, lecithin, gum acacia, cholesterol, calcium stearate, stearic acid, etc.

The capsule fill formulation may further comprise one or more disintegrants such as corn starch, potato starch, modified starches, microcrystalline cellulose, methyl cellulose, carboxymethylcelullose, sodium alginate, cellulose polyacrilin potassium, gums, agar, guar, locust bean, pectin, xanthan, agar, etc.

The capsule fill formulation may comprise one or more flow agents, or glidants to promote flowability including colloidal silica, cornstarch, talc, calcium silicate, magnesium silicate, tribasic calcium phosphate, silicon hydrogel, etc.

The capsule fill formulation may further comprise a foaming agent such as polyethylene glycol, saponin, sorbitan trioleate, sorbitan monostearate, sorbitan monopalmitate, glyceryl monostearate, and the like.

Active Agents

The capsule fill formulation may comprise any pharmacologically active agent which has a therapeutic effect when delivered vaginally.

In some embodiments, the capsule fill formulation comprises an estrogen (i.e. a natural estrogen or a synthetic compound that mimics the physiological effect of natural estrogens) including, without limitation, estradiol (17β-estradiol), estridiol acetate, estradiol benzoate, estridiol cypionate, estridiol decanoate, estradiol diacetate, estradiol heptanoate, estradiol valerate, 17α-estradiol, estriol, estriol succinate, estrone, estrone acetate, estrone sulfate, estropipate (piperazine estrone sulfate), ethynylestradiol (17α-ethynylestradiol, ethinylestradiol, ethinyl estradiol, ethynyl estradiol), ethynylestradiol 3-acetate, ethynylestradiol 3-benzoate, mestranol, quinestrol, nitrated estrogen derivatives or combinations thereof.

In other embodiments, the capsule fill formulation comprises a progestin (i.e. natural or synthetic compounds that possesses progestational activity including, without limitation, 17α-17-hydroxy-11-methylene-19-norpregna-4,15-dien-20-yn-3-one, 17α-ethynyl-19-nortestosterone, 17α-ethynyltestosterone, 17-deacetylnorgestimate, 19-nor-17-hydroxyprogesterone, 19-norprogesterone, 3β-hydroxydesogestrel, 3-ketodesogestrel (etonogestrel), acetoxypregnenolone, algestone acetophenide, allylestrenol, amgestone, anagestone acetate, chlormadinone, chlormadinone acetate, cyproterone, cyproterone acetate, d-17β-acetoxy-13β-ethyl-17α-ethynylgon-4-en-3-one oxime, demegestone, desogestrel, dienogest, dihydrogesterone, dimethisterone, drospirenone, dydrogesterone, ethisterone (pregneninolone, 17α-ethynyltestosterone), ethynodiol diacetate, fluorogestone acetate, gastrinone, gestadene, gestodene, gestonorone, gestrinone, hydroxymethylprogesterone, hydroxymethylprogesterone acetate, hydroxyprogesterone, hydroxyprogesterone acetate, hydroxyprogesterone caproate, levonorgestrel (1-norgestrol), lynestrenol (lynoestrenol), mecirogestone, medrogestone, medroxyprogesterone, medroxyprogesterone acetate, megestrol, megestrol acetate, melengestrol, melengestrol acetate, nestorone, nomegestrol, norelgestromin, norethindrone (norethisterone) (19-nor-17α-ethynyltestosterone), norethindrone acetate (norethisterone acetate), norethynodrel, norgestimate, norgestrel (d-norgestrel and dl-norgestrel), norgestrienone, normethisterone, progesterone, promegestone, quingestanol, tibolone, trimegestone, or combinations thereof.

In other embodiments, the capsule fill formulation comprises a progestin and an estrogen.

In a preferred embodiment, the active agent is a progesterone antagonist.

In one embodiment, the capsule fill formulation comprises a steroid compound disclosed in U.S. Pat. Nos. 6,861,415 and 6,900,193, the contents of which are incorporated herein by reference. In a preferred embodiment, the steroid compound is CDB-4124 (21-methoxy-17α-acetoxy-11β-(4 N,N-dimethylaminophenyl)-19-norpregna-4,9-diene-3,20-dione) or CDB-4453 (21-methoxy-17α-acetoxy-11β-(4-N-methylaminophenyl)-19-norpregna-4,9-diene-3,20-dione).

Other preferred progesterone antagonists that may be present in the capsule fill formulation include, without limitation, Mifepristone (RU-486; 11β-[4 N,N-dimethylaminophenyl]-17β-hydroxy-17-(1-propynyl)-estra-4,9-dien-3-one), Lilopristone (11β-(4 N,N-dimethylaminophenyl)-17β-hydroxy-17-((Z)-3-hydroxypropenyl)estra-4,9-dien-3-one), Onapristone (11β-(4 N,N-dimethylaminophenyl)-17α-hydroxy-17-(3-hydroxypropyl)-13α-estra-4,9-dien-3-one), asoprisnil (benzaldehyde, 4-[(11β,17β)-17-methoxy-17-(methoxymethyl)-3-oxoestra-4,9-dien-11-yl]-1-(E)-oxim; J867), its metabolite J912 (4-[17β-Hydroxy-17α-(methoxymethyl)-3-oxoestra-4,9-dien-11β-yl]benzaldehyd-(1E)-oxim) and CDB-2914 (17α-acetoxy-11β-(4-N,N-dimethylaminophenyl)-19-norpregna-4,9-dien-3,20-dione).

Other antiprogestins that may be present in the capsule fill formulation include compounds described in U.S. Pat. Nos. 4,386,085, 4,447,424, 4,536,401, 4,519,946, 4,609,651, 4,634,695, 4,780,461, 4,814,327, 4,829,060, 4,871,724, 4,921,845, 4,921,845, 5,095,129, 5,446,178, 5,478,956, 5,232,915 5,089,488, 5,093,507, 5,244,886, 5,292,878, 5,439,913, 5,446,036, 5,576,310; 5,684,151, 5,688,808, 5,693,646, 5,693,647, 5,696,127, 5,696,130, 5,696,133 5,739,125, 5,407,928, 5,273,971, 5,728,689, 5,753,655, 5,843,933, 5,843,931, 6,509,334, 6,566,358, 6,713,478, 6,391,907, 6,417,214, 6,380,235, 6,339,098, 6,306,851, 6,441,019, 6,369,056, and 6,358,948, the contents of each of which are incorporated herein by reference.

Other antiprogestins that may be useful in the invention include, without limitation JNJ-1250132, (6α,11β,17β)-11-(4-dimethylaminophenyl)-6-methyl-4',5'-dihydrospiro[estra-4,9-diene-17,2'(3'H)-furan]-3-one (ORG-31710); (11β,17α)-11-(4-acetylphenyl)-17,23-epoxy-19,24-dinorchola-4,9,20-trien-3-one (ORG-33628); (7β,11β,17β)-11-(4-dimethylaminophenyl-7-methyl]-4',5'-dihydrospiro[estra-4,9-diene-17,2'(3'H)-furan]-3-one (ORG-31806); ZK-112993; ORG-31376; ORG-33245; ORG-31167; ORG-31343; RU-2992; RU-1479; RU-25056; RU-49295; RU-46556; RU-26819; LG1127; LG120753; LG120830; LG1447; LG121046; CGP-19984A; RTI-3021-012; RTI-3021-022; RTI-3021-020; RWJ-25333; ZK-136796; ZK-114043; ZK-230211; ZK-136798; ZK-98229; ZK-98734; ZK-137316; 4-[17β-Methoxy-17α-(methoxymethyl)-3-oxoestra-4,9-dien-11β-yl]benzaldehyde-1-(E)-oxime; 4-[17β-Methoxy-17α-(methoxymethyl)-3-oxoestra-4,9-dien-11β-yl]benzaldehyde-1-(E)-[O-(ethylamino)carbonyl]oxime; 4-[17β-Methoxy-17α-(methoxymethyl)-3-oxoestra-4,9-dien-11β-yl]benzaldehyde-1-(E)-[O-(ethylthio)carbonyl]oxime; (Z)-6'-(4-cyanophenyl)-9,11α-dihydro-17β-hydroxy-17α-[4-(1-oxo-3-methylbutoxy)-1-butenyl]4'H-naphtho[3',2',1';10,9,11]estr-4-en-3-one; 11β-(4-acetylphenyl)-17β-hydroxy-17α-(1,1,2,2,2-pentafluoroethyl)estra-4,9-dien-3-one; 11beta-(4-Acetylphenyl)-19,24-dinor-17,23-epoxy-17alpha-chola-4,9,20-trien-3-one; (Z)-11beta,19-[4-(3-Pyridinyl)-o-phenylene]-17beta-hydroxy-17α-[3-hydroxy-1-propenyl]-4-androsten-3-one; 11beta-[4-(1-methylethenyl)phenyl]-17α-hydroxy-17beta-(3-hydroxypropyl)-13α-estra-4,9-dien-3-one; 4',5'-Dihydro-11beta-[4-(dimethylamino)phenyl]-6beta-methylspiro[estra-4,9-dien-17beta,2'(3'H)-furan]-3-one.

In related aspects, capsule fill formulations comprise a pharmaceutically acceptable salt of a pharmaceutically active compound such as an antiprogestin. Depending on the process conditions the salt compound obtained may be either in neutral or salt form. Salt forms include hydrates and other solvates and also crystalline polymorphs. Both the free base and the salts of these end products may be used in accordance with the invention. Acid addition salts may in a manner known per se be transformed into the free base using basic agents such as alkali or by ion exchange. The free base obtained may also form salts with organic or inorganic acids.

In the preparation of acid addition salts, preferably such acids are used which form suitably pharmaceutically acceptable salts. Examples of such acids are hydrochloric acid, sulfuric acid, phosphoric acid, nitric acid, aliphatic acid, alicyclic carboxylic or sulfonic acids, such as formic acid, acetic acid, propionic acid, succinic acid, glycolic acid, lactic acid, malic acid, tartaric acid, citric acid, ascorbic acid, glucuronic acid, fumaric acid, maleic acid, hydroxymaleic acid, pyruvic acid, aspartic acid, glutamic acid, p-hydroxybenzoic acid, embonic acid, ethanesulfonic acid, hydroxyethanesulfonic acid, phenylacetic acid, mandelic acid, alogenbensenesulfonic acid, toluenesulfonic acid, galactaric acid, galacturonic acid or naphthalenesulfonic acid. All crystalline form polymorphs may be used in accordance with the invention.

Base addition salts may also be used in accordance with the invention and may be prepared by contacting the free acid form with a sufficient amount of the desired base to produce the salt in the conventional manner. The free acid form may be regenerated by contacting the salt form with an acid and isolating the free acid in the conventional manner. Pharmaceutically acceptable base addition salts are formed with metals or amines, such as alkali and alkali earth metals or organic amines Examples of metals used as cations are sodium, potassium, calcium, magnesium and the like. Examples of suitable amines are amino acids such as lysine, choline, diethanolamine, ethylenediamine, N-methylglucamine and the like.

Disorders that May be Treated by Vaginal Delivery of Pullulan Capsules

Pullulan capsules comprising a fill formulation comprising a pharmaceutically active agent may be administered to the vagina of a subject to treat a variety of disorders or achieve a variety of desired therapeutic results in a subject. Preferably the subject is a female mammal, most preferably a human female.

In some embodiments of the invention, a pullulan capsule comprising a pharmaceutically active compound is administered to a female patient in need thereof in order to treat a disorder selected from the group consisting of endometrial hyperproliferation, endometriosis (or pain associated therewith), dysmenorrhea, uterine fibroids, adenomyosis, endometrioma, ovarian cancer, cervical cancer. In a preferred embodiment, endometriosis, dysmennorhea, uterine fibroids, adenomyosis, ovarian cancer or cervical cancer is treated by administering an intravaginal preparation containing a compound of general formula I to the vagina of a patient in need of such treating.

In another embodiment of the invention, a pullulan capsule of the invention is administered to a female in need thereof in order to induce menses in the female in which case the capsule fill formulation preferably comprises a progestin such as medroxyprogesterone 17-acetate.

In yet another embodiment of the invention, a pullulan capsule of the invention is administered to a female in need thereof in order to induce labor.

In yet another embodiment of the invention, a pullulan capsule of the invention is administered to a female in need thereof as a contraceptive, in which case the capsule fill formulation preferably comprises a progestin and optionally an estrogen.

Dosages and Administration Regimens

A therapeutically effective amount of an active agent required for use in therapy varies with the length of time that activity is desired, and the age and the condition of the patient to be treated, among other factors, and is ultimately determined by the attendant physician. In general, however, doses employed for human treatment typically are in the range of about 0.001 mg/kg to about 500 mg/kg per day, for example about 1 µg/kg to about 1 mg/kg per day or about 1 µg/kg to about 100 µg/kg per day. For most large mammals, the total daily dosage is from about 1 to 100 mg, preferably from about 2 to 80 mg. The dosage regimen may be adjusted to provide the optimal therapeutic response. The desired dose may be conveniently administered in a single dose, or as multiple doses administered at appropriate intervals, for example as two, three, four or more subdoses per day.

Illustratively, a pullulan capsule of the invention may be vaginally administered to a subject to provide the subject with an active agent such as an antiprogestin in an amount of about 1 µg/kg to about 1 mg/kg body weight, for example about 1 µg/kg, about 25 µg/kg, about 50 µg/kg, about 75 µg/kg, about 100 µg/kg, about 125 µg/kg, about 150 µg/kg, about 175 µg/kg, about 200 µg/kg, about 225 µg/kg, about 250 µg/kg, about 275 µg/kg, about 300 µg/kg, about 325 µg/kg, about 350 µg/kg, about 375 µg/kg, about 400 µg/kg, about 425 µg/kg, about 450 µg/kg, about 475 µg/kg, about 500 µg/kg, about 525 µg/kg, about 550 µg/kg, about 575 µg/kg, about 600 µg/kg, about 625 µg/kg, about 650 µg/kg, about 675 µg/kg, about 700 µg/kg, about 725 µg/kg, about 750 µg/kg, about 775 µg/kg, about 800 µg/kg, about 825 µg/kg, about 850 µg/kg, about 875 µg/kg, about 900 µg/kg, about 925 µg/kg, about 950 µg/kg, about 975 µg/kg or about 1 mg/kg body weight.

Pharmaceutically active compounds are present in the capsule fill formulation at a therapeutically effective dose that is preferably lower compared to the therapeutically effective dose of the compound when administered orally. For example, the therapeutically effective dose may be less than 50 mg/day, less than 40 mg/day, less than 30 mg/day less than 20 mg/day, less than 10 mg/day, less than 5 mg/day, less than 3 mg/day, between 1 mg/day and 50 mg/day, between 3 mg/day and 40 mg/day, between 3 mg/day and 30 mg/day, between 3 mg/day and 20 mg/day, between 3 mg/day and 10 mg/day, between 5 mg/day and 20 mg/day or between 5 mg and 10 mg/day. In other embodiments, the effective dose may be 3 mg per day to 12 mg/day, 5 mg/day to 12 mg/day, or 12 mg/day to 25 mg/day. In other embodiments, the effective dose is 1 or 1.5 mg/day, 2 or 2.5 mg/day, 3 or 3.5 mg/day, 4 or 4.5 mg/day 5 or 5.5 mg/day, 6 or 6.5 mg/day, 7 or 7.5 mg/day, 8 or 8.5 mg/day, 9 or 9.5 mg/day, 10 or 10.5 mg/day, 11 or 11.5 mg/day, 12 or 12.5 mg/day, 13 or 13.5 mg/day, 14 or 14.5 mg/day, 15 or 15.5 mg/day, 16 or 16.5 mg/day, 17 or 17.5 mg/day, 18 or 18.5 mg/day, 19 or 19.5 mg/day, 20 or 20.5 mg/day, 21 or 21.5 mg/day, 22 or 22.5 mg/day, 23 or 23.5 mg/day, 24 or 24.5 mg/day or 25 or 25.5 mg/day. In another related embodiment, the effective amount of the compound in the capsule fill formulation is 2-fold, 3-fold, 4-fold 5-fold, 6-fold, 7-fold, 8-fold, 9-fold and even 10-fold less than the effective amount when administered systemically to treat endometriosis, uterine fibroids and other diseases located in that region.

Pullulan capsules comprising a fill formulation comprising an active agent, as described above, are suitable for prolonged/chronic vaginal administration because these compounds are expected to exhibit low systemic concentrations and therefore little or no liver toxicity. In one embodiment, the pullulan capsules are administered for an administration period of least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31 or more days. The capsules may also be administered for an administration period of least 1, 2, 3, 4, 5, 6, 7, 8, 9, 10, 11, 12 or more months. The capsules may also be administered for an administration period of at least 1, 2, 3, 4, 5, 6, 7, 8, 9, 10 or more years. During the administration period, the capsules may be administered daily or periodically such as every other day, every other month, and the like but are preferably administered once per day. The capsules may also be administered intermittently. For example, the capsules may be administered for an administration period of 1, 2, 3, 4, 5 or more months, followed by a period of discontinuance, followed by an administration period of 1, 2, 3, 4, 5 or more months, and so on.

In one embodiment, the capsule is administered intermittently such that the subject undergoes menses during at least one discontinuance period. This approach is expected to avoid the adverse effects associated with a thickened or stagnant endometrium that may accompany extended treatment with progesterone antagonists, such as spotting, breakthrough bleeding, endometrial hyperproliferation or endometrial cancer. At least one, and preferably every discontinuance period is of sufficient length for the subject to experience menstruation. More preferably, the subject experiences menstruation during every discontinuance period. In a particularly preferred embodiment, the capsule is administered daily for an administration period of four months, followed by a discontinuance period during which the subject experiences menstruation, followed by another administration period of four months and so on.

Patients undergoing treatments with the compositions of the instant invention should be monitored routinely for their serum estrogen and glucocorticoid levels.

The following non-limiting examples are provided to aid in understanding the teachings of the instant invention.

EXAMPLE 1

Preparation of Pullulan Capsules Comprising the Selective Progesterone Receptor Modulator CDB-4124

The following capsule fill formulations (without active agent) were liquified at 50-70° C. for liquid fill into capsules or molded into vaginal "tablets" as described below:

| | |
|---|---|
| Gelucire 44/14 | 74.13% (excipient w/w) |
| PEG 400 | 25.87% (excipient w/w) |
| Wecobee M | 50.1% (excipient w/w) |
| PEG 1000 | 49.4% (excipient w/w) |
| Lecithin | 0.5% (excipient w/w) |
| PEG1000 | 100% or 99.98% (excipient w/w) |
| Butylated hydroxytoluene | 0% or 0.02% (excipient w/w) |

The fill formulations were used to fill several kinds of capsules including regular gelatin capsules, soft-gel capsules, and pullulan capsules (Capsugel NPcaps®) or were molded into uncoated vaginal "tablets" in order to test the suitability of the different types of capsules or "tablets" as vaginal delivery vehicles.

First, standard gelatin capsules were filled with the above fill formulations, wrapped with moist paper towels and incubated in an oven at 38° C. to simulate vaginal conditions. Standard gelatin capsules were determined to be unacceptable vaginal delivery vehicles in part due to the length of time necessary for the capsules to soften and release the drug. Moreover, residual capsule shells will remain in the vagina and need to be washed out after administration of drug. In addition to these shortcomings, it was determined that the pills generally would not adhere to the vaginal mucosa. Accordingly, standard gelatin capsules were determined to be unacceptable vaginal delivery vehicles.

Next, the fill formulation was molded into uncoated "tablets" using a bullet-shaped plastic mold to compress the fill and an applicator was used to deliver the drug. The uncoated bullet shaped tablets were administered vaginally to human females with uterine fibroids. This method of vaginal administration was determined to be impractical due to handling concerns (the material would often melt during handing prior to administration and also because a commercial scale process for filling the bullet shaped mold was not available.

Standard soft-gel capsules were also tried, but were found to have the same problems as the gelatin capsules.

Finally, Capsugel NPcaps® were tested as a potential vaginal delivery vehicle and were determined to be potentially advantageous as the capsules dissolved in the uterus after a period of time and adhered to the vaginal mucosa.

EXAMPLE 2

Pharmacokinetic Animal Studies of Vaginal Delivery of the Selective Progesterone Receptor Modulator CDB-4124

Pullulan capsules (Capsugel NPcaps®, size 0) comprising CDB-4124 were administered once daily for 10 consecutive days intravaginally to 10 healthy virgin female New Zealand White rabbits in order to determine the cumulative vaginal mucous membrane irritancy potential and to obtain plasma samples for pharmacokinetic analysis. Five rabbits were assigned to each of two groups, the first dosed with vehicle control (pullulan capsules with 0.5 ml PEG 1000 fill) introduced into the upper vaginal vault of each rabbit using a syringe applicator (Group 1), the second with CDB-4124 (pullulan capsules with 12 mg CDB-4124 in 0.5 ml PEG 1000)(Group 2). The external vaginal mucosa of each animal was examined for erythema, edema and discharge prior to the initial dose, immediately prior to each treatment and prior to sacrifice. All animals were examined for gross pathology.

All animals survived to the end of the study. The external vaginal mucosa of all Group 1 animals appeared normal during the study and no abnormal physical signs were noted for any animal during the study. The external vaginal mucosa of ⅖ rabbits showed very slight erythema and/or edema on 4 occasions and appeared normal otherwise. No gross findings were noted in the ovaries, uterus, or three sections of the vagina in either group, nor were any histopathological findings observed in either group. The irritation index was considered to be "none". The data confirms that pullulan capsules are a safe delivery vehicle for administering active agents and can be safely used for local vaginal delivery of CDB-4124 with minimal vaginal irritation.

Figure 4:
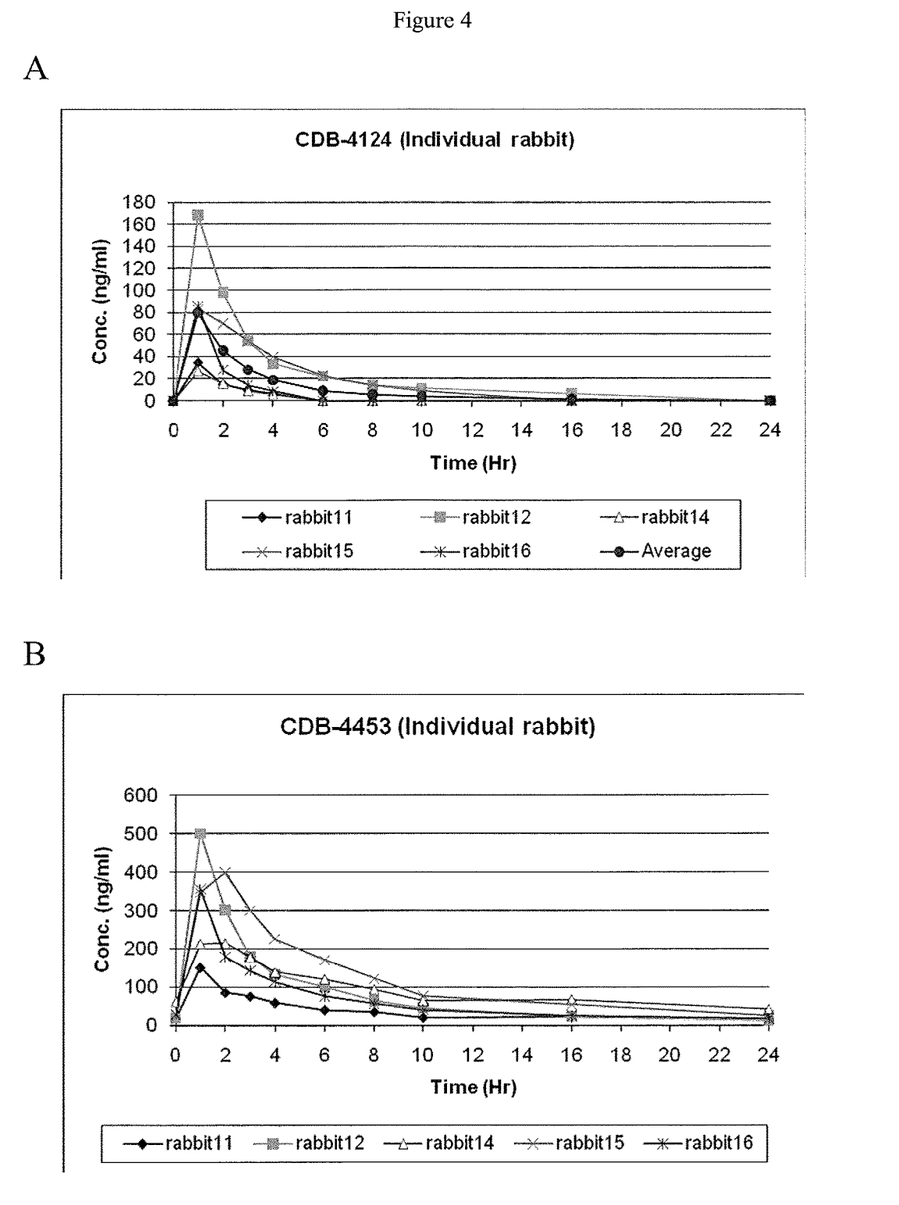

Samples (0.4 ml blood) for evaluation of pharmacokinetics were collected from each rabbit in Group 2 prior to dosing on the last day (10th dose) and at 1, 2, 3, 4, 6, 7, 10, 16 and 24 hours following the last dose administration. Average pharmacokinetic data is shown in Table 1 below. A graph depicting data from individual rabbits is illustrated at FIG. 4A-B.

TABLE 1

| Pharmacokinetic Data (Group II - 5 rabbits) | | |
|---|---|---|
| Time (hr) | Average | S.D. |
| CDB-4124 | | |
| 0 | 0.00 | 0.00 |
| 1 | 79.62 | 56.32 |
| 2 | 45.22 | 36.95 |
| 3 | 27.98 | 23.67 |
| 4 | 18.69 | 16.42 |
| 6 | 8.88 | 12.16 |
| 8 | 5.66 | 7.75 |
| 10 | 3.94 | 5.48 |
| 16 | 1.34 | 2.99 |
| 24 | 0.00 | 0.00 |
| AUC | 235.06 | 209.59 |
| Cmax | 79.66 | 56.32 |
| CDB-4453 | | |
| 0 | 30.88 | 17.90 |
| 1 | 313.80 | 136.37 |
| 2 | 236.06 | 119.92 |
| 3 | 175.10 | 81.51 |
| 4 | 133.88 | 60.43 |
| 6 | 101.46 | 49.12 |
| 8 | 74.10 | 34.22 |
| 10 | 49.18 | 21.97 |
| 16 | 38.14 | 20.99 |
| 24 | 21.98 | 11.91 |
| AUC | 1843.98 | 715.19 |
| CMAX | 324.60 | 141.37 |

EXAMPLE 3

Vaginal Administration of Pullulan Capsules Comprising CDB-4124

Figure 5:
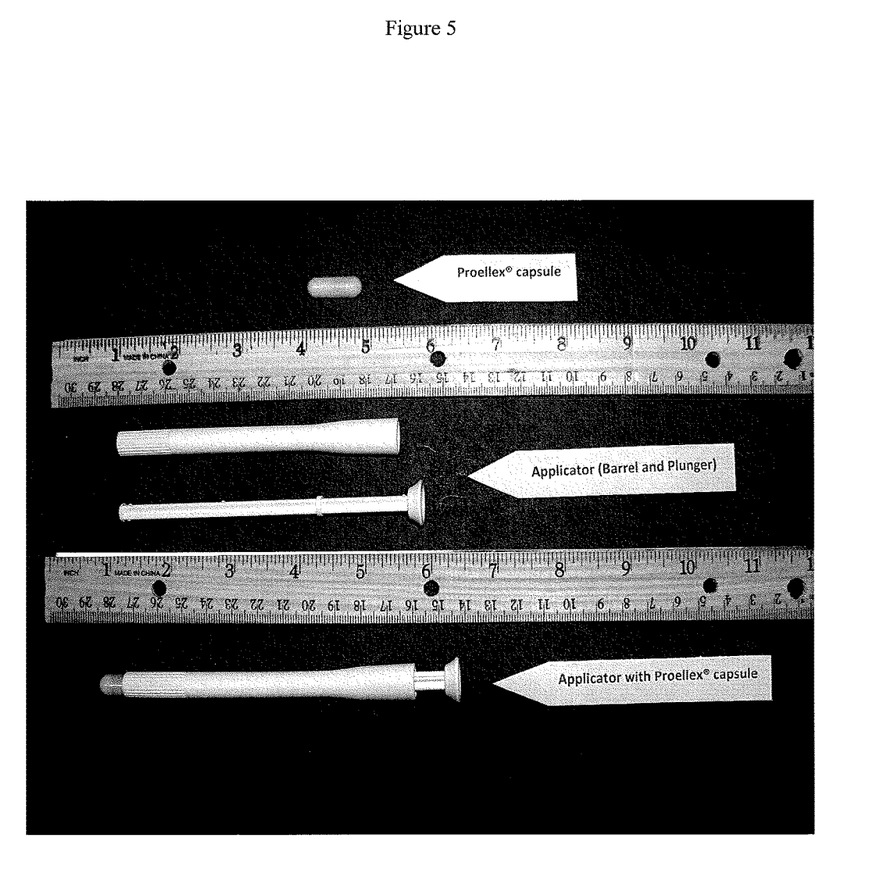
FIG. 5 illustrates the applicator used to vagnially deliver pullulan capsules comprising 12 mg CDB-4124 to human females.

Capsugel NPcaps® were filled with the excipient fill formulations described above with 12 mg CDB-4124 (telapristone acetate) and administered vaginally to human females with uterine fibroids once per day for a period of 2 weeks to determine the length of time required to reach steady state and overall systemic exposure of the parent compound (CDB-4124) and the primary metabolite (CDB-4453). The capsules were administered using a commercially available vaginal applicator modified by reversing the insert (see FIG. 5). The unmodified applicator comprises a barrel and plunger with the barrel having a relatively wide opening on one end and a relatively narrow opening on the other end. The applicator is designed such that the drug is placed in the end with the larger diameter opening (entrance end), the applicator is inserted into the vagina and the plunger is used to push the drug out the barrel and into the vagina. For insertion of the filled NPcaps, the shell end of the capsule (having a slightly larger diameter) was placed into the narrow opening in the barrel, leaving the cap exposed. The NPcaps were found to adhere to the vaginal mucosa immediately upon insertion, so patients were advised of the importance of ensuring that the capsule be positioned properly before capsule release. Pharmacokinetic data was then obtained from patients.

Figure 1:
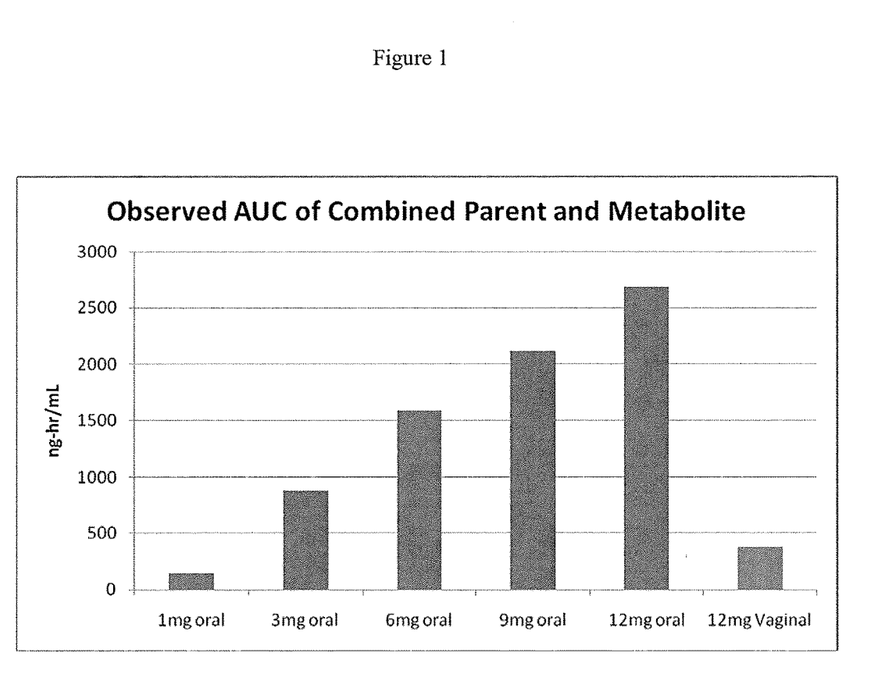
FIG. 1 illustrates the area under the curve (AUC) of CDB-4124 and its monodemethylated metabolite CDB-4453, following administration of CDB-4124 to human females with uterine fibroids at 1 mg, 3 mg, 6 mg, 9 mg and 12 mg oral doses compared with vaginal administration of a 12 mg dose.
Figure 2:
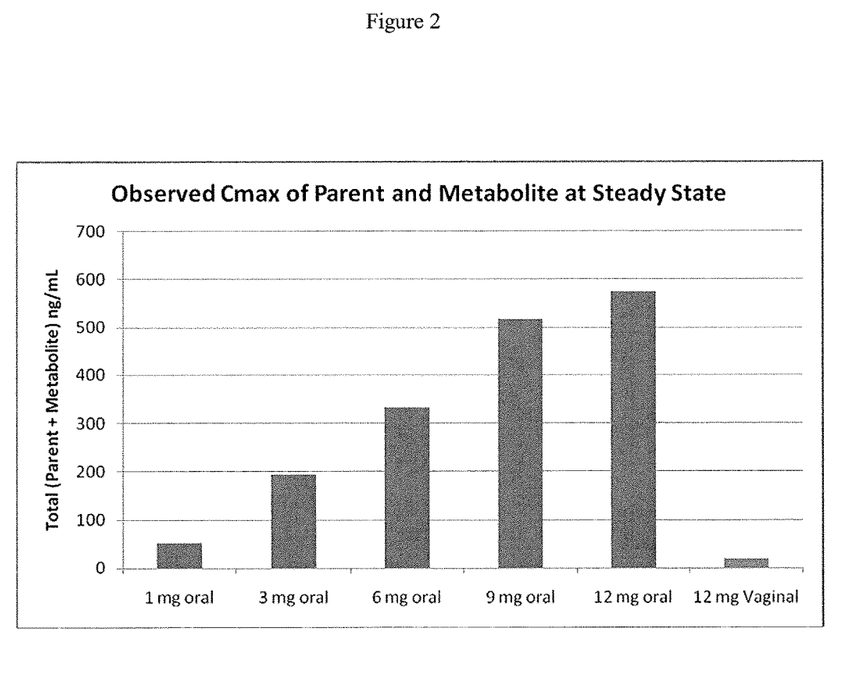
FIG. 2 illustrates a comparison of the Cmax (peak serum concentration) of CDB-4124 and CDB-4453 following 1 mg, 3 mg, 6 mg, 9 mg, and 12 mg oral doses to human females with uterine fibroids compared with vaginal administration of a 12 mg dose.
Figure 3:
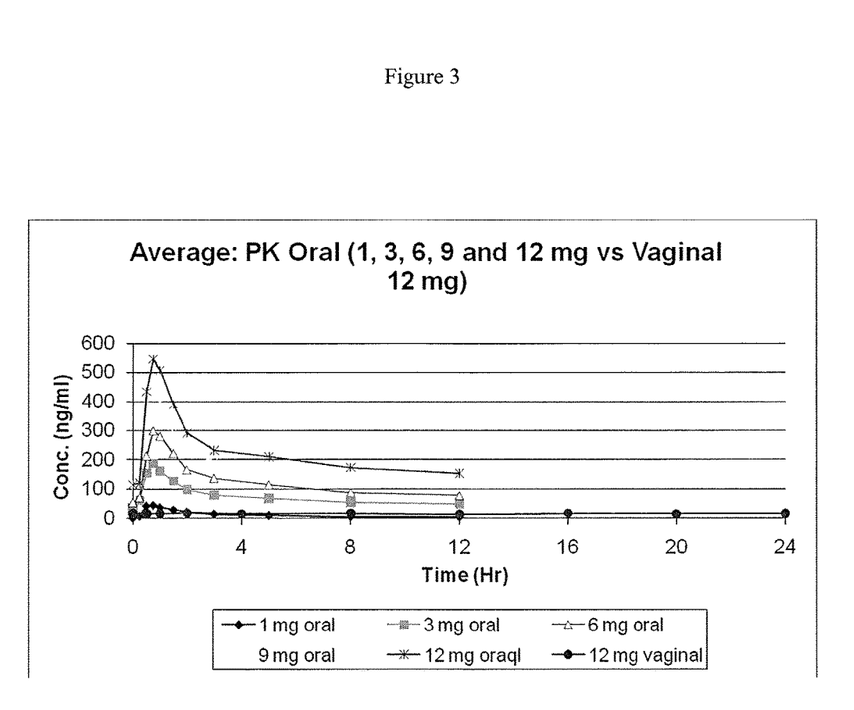
FIG. 3 illustrates pharmacokinetic data observed at steady state over a 24 hour period following administration of 1 mg, 3 mg, 6 mg, 9 mg and 12 mg oral versus 12 mg vaginal doses of CDB-4124.

Steady state concentration of the drug appeared to be achieved within one week of administration, after which there was no obvious drug peak as observed in other delivery methods and in contrast to the same formulation in dogs and rabbits where a drug peak was observed several hours after delivery. As illustrated at FIG. 1, vaginal administration of pullulan capsules comprising CDB-4124 resulted in about ⅙th the systemic exposure of an equivalent oral dose based on area under the curve (AUC). Cmax on the other hand, as illustrated in FIG. 2, was lower than any of the oral doses. As illustrated in FIG. 3, pullulan capsules comprising CDB-4124 effect a continuous release of active agents at a substantially constant rate without the high Cmax observed upon oral administration of the drug.

In a previous oral study, doses of 1, 3, 6, 9 and 12 mg of CDB-4124 were administered for a period of 10 weeks. In the oral study, all doses were well tolerated and reliable cessation of menses was induced at doses as low as 3 mg. Cessation of menses directly correlates to efficacy of an oral dose in both uterine fibroids and endometriosis. Remarkably a vaginal dose of 12 mg, despite achieving only a fraction of the exposure of the ineffective 1 mg oral dose, resulted in cessation of menses in 3 of the women. Statistical significance ($p<0.05$) was seen in a pair-wise comparison of the 6 women from both the perspective of reduction in menstrual bleeding using the Pictorial Blood Loss Assessment Chart (PBAC) and also the reduction in overall uterine fibroid symptoms as determined by the Uterine Fibroid Symptom Quality of Life Survey (UFSQOL). Given the overall low exposure of the 12 mg dose, in those women that continued to menstruate, further improvements in reduction of symptoms are expected with longer exposure to the drug. In efficacy studies in which CDB-4124 was administered orally, women experienced a nearly 50% reduction in mean fibroid size at a 25 mg dose. When those women were then escalated to a 50 mg oral dose for an additional four months, fibroid size was reduced to approximately 25% of the initial volume. Based on the assessment of fibroid symptoms as scored by UFSQOL, women on oral CDB-4124 were, in general, symptom free. It is expected that vaginal delivery of CDB-4124 at the 12 mg dose will have greater activity than the oral 50 mg dose despite a maximum exposure 1/100th of the 50 mg oral dose. Even with this low exposure after only 4 weeks of treatment, significant improvements in fibroid related condition have been observed.

Accordingly, administration of pullulan capsules provide a means for delivering sustained levels of active agent to the vaginal mucosa while minimizing systemic exposure of the drugs.

What is claimed is:

1. A method for treating a progesterone-dependent condition in a human female comprising administering to the vaginal mucosa of the female a mucoadhesive capsule comprising:
   85 to 90 wt % pullulan; potassium chloride in an amount of 1.0% to 1.5% by weight; carrageenan in an amount of 0.1% to 0.4% by weight; one or more surfactants in an amount of 0.1 to 0.2% by weights; and water; and
   a fill formulation comprising the antiprogestin CDB-4124, and excipients comprising 30% to 60% w/w fatty acid esters, 30% to 60% w/w PEG 1000 and 0.1 to 5% w/w lecithin;
   wherein the progesterone-dependent condition is selected from the group consisting of endometriosis, adenomyosis, edometriomas of the ovary, dysmenorrhea, uterine fibroids, endometrial hyperproliferation, ovarian cancer, and cervical cancer.

2. The method of claim 1, wherein the antiprogestin CDB-4124 is administered daily at a dosage of 1 mg to 50 mg.

3. The method of claim 2, wherein the antiprogestin CDB-4124 is administered at a dosage of 12.5 mg or less.

4. The method of claim 3, wherein the capsule comprises pullulan in an amount of 86.3% by weight, potassium chloride in an amount of 1.32% by weight, carrageenan in an amount of 0.27% by weight, surfactants selected from sugar esters, sorbitan monolaurate and combinations thereof in an amount of 0.15% by weight and water.

5. The method of claim 4, wherein the fill formulation consists essentially of the antiprogestin CDB-4124 and PEG 1000, and optionally butylated hydroxytoluene.

6. The method of claim 4, wherein the capsule is administered once per day.

* * * * *